United States Patent [19]

Fuhrmann et al.

[11] Patent Number: 5,002,576
[45] Date of Patent: Mar. 26, 1991

[54] INTERVERTEBRAL DISK ENDOPROSTHESIS

[75] Inventors: Gerhard Fuhrmann; Ulrich Gross; Bertram Kaden; Herman-Josef Schmitz; Thomas Fritz; Curt Kranz, all of Berlin, Fed. Rep. of Germany

[73] Assignee: Mecron Medizinische Produkte GmbH, Berlin, Fed. Rep. of Germany

[21] Appl. No.: 362,153

[22] Filed: Jun. 6, 1989

[30] Foreign Application Priority Data

Jun. 6, 1988 [DE] Fed. Rep. of Germany ....... 8807485

[51] Int. Cl.⁵ ................................. A61F 2/44
[52] U.S. Cl. ......................... 623/17; 606/61
[58] Field of Search ................ 623/17, 22, 23; 606/61

[56] References Cited

U.S. PATENT DOCUMENTS

| 3,867,728 | 2/1975 | Stubstad | 623/17 |
| 3,875,595 | 4/1975 | Froning | 623/17 |
| 4,349,921 | 9/1982 | Huntz | 623/17 |
| 4,772,287 | 9/1988 | Ray et al. | 623/17 |
| 4,932,975 | 6/1990 | Main et al. | 623/17 |

FOREIGN PATENT DOCUMENTS

| 0176728 | 4/1986 | European Pat. Off. | |
| 0179695 | 4/1986 | European Pat. Off. | 623/17 |
| 0277282 | 8/1988 | European Pat. Off. | 623/17 |
| 0317972 | 5/1989 | European Pat. Off. | 623/17 |
| 2263842 | 7/1974 | Fed. Rep. of Germany | |
| 2203242 | 3/1975 | Fed. Rep. of Germany | 623/17 |
| 2821678 | 4/1980 | Fed. Rep. of Germany | |
| 3529761 | 7/1986 | Fed. Rep. of Germany | |
| 239523 | 10/1986 | Fed. Rep. of Germany | |
| 8711992 | 11/1987 | Fed. Rep. of Germany | |

OTHER PUBLICATIONS

Von K. Roosen, W. Grote, A. Trauschel, "Dorsale Verklammerungsspondylodese der oberen Halswirbelsaule ein neues technisches Konzept" [A New Method of Dorsal Fusion by Staples of the Upper Cervical Spine], med.-orthop.-Techn., 1/83, pp. 18–21.

P. G. Schneider, R. Oyen, "Bandscheibenersatz Experimentelle Untersuchungenklinische Konseguenzen" Vertebral Disc Replacement Experimental Studies Clinical Findings, Z. Orthop. 112, 1974, pp. 791–795.

Primary Examiner—Randall L. Green
Assistant Examiner—David H. Willse
Attorney, Agent, or Firm—Spencer & Frank

[57] ABSTRACT

An intervertebral disk endoprosthesis is filled with an elastic material and provided with cover plates at its end faces, and has a circular or elliptical corrugated tube surrounding the viscoelastic material, the tube being terminated by cover plates.

21 Claims, 2 Drawing Sheets

INTERVERTEBRAL DISK ENDOPROSTHESIS

CROSS REFERENCE TO RELATED APPLICATION

This application claims the priority of application Ser. No. G 88 07 485,4, filed June 6, 1988, in the Federal Republic of Germany, the subject matter of which is incorporated herein by reference.

BACKGROUND OF THE INVENTION

The present invention relates to an endoprosthesis of the type filled with viscoelastic material and provided with cover plates at its end faces German Pat. No. 2,203,242 discloses such a prosthesis.

Its drawback is that the elastic material applied between the cover plates is not completely compatible with the human body since harmful long-term reactions with the surrounding body tissue cannot be permanently excluded.

Moreover, DE-OS 3,529,761, which corresponds to U.S. Pat. No. 4,759,766, discloses an intervertebral disk prosthesis in which a rigid spacer is provided between two symmetrical end plates. The end plates are movable relative to one another by the interaction of meshing pairs of convex and concave faces.

Here again there exists the drawback that the surfaces rubbing against one another create abrasion particles.

SUMMARY OF THE INVENTION

It is the object of the present invention to provide an endoprosthesis of the above-mentioned type in which better compatibility with the human body is provided and which additionally prevents material particles from being released due to frequent alternating stresses and moving around.

This object and others to become apparent as the specification progresses, are accomplished by the invention, according to which, briefly stated, an intervertebral disk endoprosthesis filled with viscoelastic material and provided with cover plates at its end faces, has a circular or elliptical corrugated tube surrounding and contiguous with the viscoelastic material and terminated by the cover plates.

The invention is based on the realization that a cuff in the form of a corrugated tube, preferably made of titanium, surrounding the viscoelastic material, on the one hand, provides a body-compatible exterior surface and, on the other hand, a hermetically sealing inclusion.

The corrugated tube is here preferably incorporated in the elastic properties in such a manner that it prevents excessive bulging of the interior body upon compression and thus contributes to its form stability. In particular, the suppression of bulging also prevents painful contact with adjacent nerves.

By filling the viscoelastic material entirely or partially with oriented or unoriented fibers, the viscosity of the elastic interior body can be controlled. An increase in the degree of fill reduces compressibility. The arrangement, which is oriented perpendicularly to the direction of the load and perpendicularly to the direction of the gradient of fill level changes, curves under a load. Suitable distribution, for example by increasing the degree of fill in the center, also permits the creation of an arrangement in which the frontal faces form a type of "rocker" which is able to tilt to all sides. With an asymmetrical arrangement of the filling, an asymmetrical, preferential tilting or pushing behavior can also be realized.

In particular, the viscoelastic material filling the corrugated tube is composed of a polymerizable material which is introduced in liquid form into a fill opening during manufacture. Additionally, there is advantageously provided a ventilating opening. A silicone adhesive as it is employed to glue together blood vessels is particularly suitable as the viscoelastic material.

The endoprosthesis according to the invention is preferably employed in such a manner that the adjacent vertebrae are milled down so that the then exposed spongy tissue grows into regions of the cover plates which are provided with a porous and particularly bioactive surface.

Screw-type clamping devices or weld connections are favorable for fastening the cover plates and the corrugated tube. A connection by means of a tension ring is also of advantage.

According to a first advantageous embodiment, the intervertebral disk endoprosthesis is composed of a closed spring body which is filled in its interior with a viscoelastic material that is reinforced with fibers to different degrees. At both its ends, the spring body is sealingly and firmly connected with planar cover plates made of a bioactive material.

In another embodiment, the intervertebral disk endoprosthesis is composed of a closed spring body which is filled in its interior with a viscoelastic material that is reinforced with fibers to different degrees in different areas. At both its ends, this spring body is also sealingly and firmly connected with rigid cover plates whose surfaces are adapted to the vertebrae and are provided with laterally disposed tabs for the accommodation of fastening screws that act as tension screws.

Advantageous modifications of the invention are defined in the dependent claims and will be described in greater detail below in connection with a description of the preferred embodiment of the invention and with reference to the drawing figures.

DETAILED DESCRIPTION OF THE PREFERRED EMBODIMENTS

Figure 1:
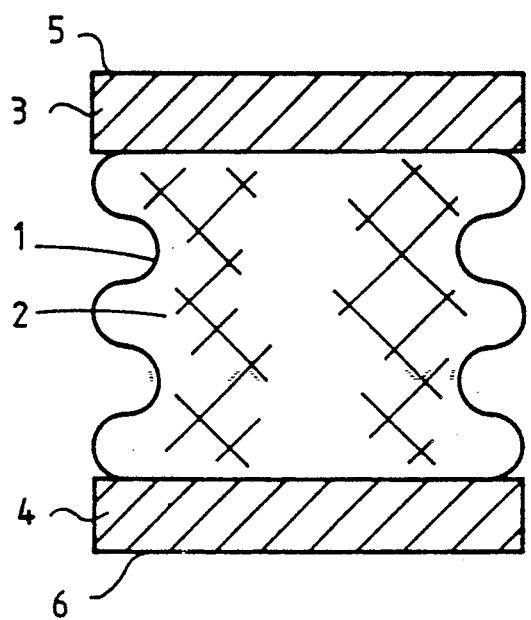
FIG. 1 is an enlarged side view of a first embodiment of the invention.

In the first embodiment shown in FIG. 1, the intervertebral disk endoprosthesis is composed of a spring body in the form of a closed corrugated tube 1 filled in its interior with a viscoelastic material 2 and sealingly and firmly connected at both its ends with planar cover plates 3 and 4 of a bioactive material or a material provided with a bioactive coating. In principle, the corrugated tube is similar to corresponding spring elements as they are employed in barometric pressure gauges or the like.

The viscoelastic material is preferably composed of body-compatible silicone. Thus the spring body forms a stable buffer element which can be compressed and deformed without its axial cross section changing substantially since it is enclosed by the flexible corrugated tube. However, in addition to compressive movements, tilting, shear and, to a limited extent, also torsional movements are possible without the cross section of the spring body being enlarged. The spring body is stable with respect to its surface characteristics and is not subject to any wear. In order to adapt the implants to special requirements, it is provided that the elasticity characteristics of material 2 and possibly also of corrugated tube 1 differ locally. For this purpose, a variable fiber reinforcement is provided for material 2 which locally changes its compressibility in such a way that compression causes a "rolling off" to the region equipped with the fiber fill. Local weakening of the corrugated tube surrounding the filling serves to further augment this effect caused by the inhomogeneity of the spring body. The exterior faces 5 and 6 of cover plates 3 and 4 are either adapted to the shape of the adjacent natural vertebrae or are made planar. Faces 5 and 6 are provided with a bioactive coating—not shown in detail—which enhances the in-growth of body tissue. Such coatings are hydroxyl apatite, ceramic HIP material or polylactide. Resorbable material is preferably applied into secondary pores to which the bone grows once the resorbable material has been catabolized. This also suppresses infections. A porous surface of the metallic basic body of cover plates 3 and 4 can be realized, for example, by sand-blasting. The in-growth of the vertebrae is enhanced by milling down the bone surface so that the spongy tissue is exposed and a—preferably planar—contact surface on the bone is available which is adapted to faces 5 and 6, respectively. The metallic components of the implant are uniformly made of titanium (or some other suitable material, such as stainless steel suitable for implantation purposes) so as to ensure the best possible body compatibility and exclude corrosion.

Figure 2:
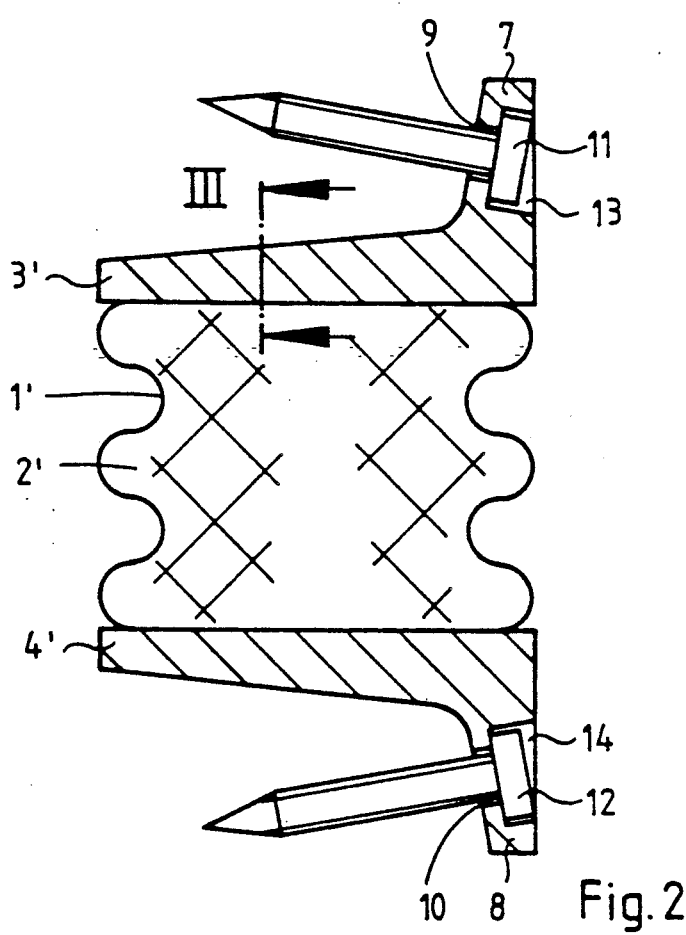
FIG. 2 is a corresponding illustration of a second embodiment.

In a second embodiment which is illustrated in FIG. 2, the intervertebral disk endoprosthesis is again composed of a closed spring body in the form of a corrugated tube 1' which is filled in its interior with a viscoelastic material 2' that is reinforced with fibers to different degrees and is sealingly and firmly closed at both its ends by means of rigid cover plates 3' and 4'. Laterally disposed, tab-like flanges 7 and 8 are connected with cover plates 3' and 4' and are oriented perpendicularly to the surfaces of the cover plates. The flanges are provided with holes 9 and 10 for the passage of bone screws 11 and 12. The holes are oriented in such a way that screws 11 and 12 inserted from the outside spread open in the screw-in direction and thus constitute tension screws for cover plates 3' and 4'. Holes 9 and 10 are provided with widened portions 13 and 14 to accommodate the heads of conventional bone screws so that the latter can be countersunk. By means of flanges 7 and 8 and bone screws 11 and 12, the implants are screwed onto the vertebrae from the front. The bone screws are also composed of the metallic material of the remainder of the implant.

Figure 3:
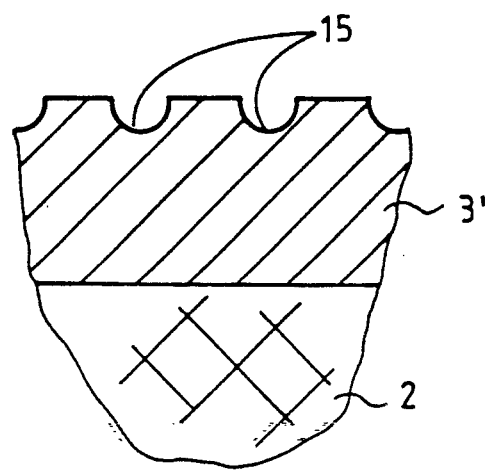
FIGS. 3 and 4 are enlarged detail views of variations of the embodiment.

The variation of the embodiment shown in FIG. 3 is an enlarged detail of the embodiment of FIG. 2 seen along the section line marked III in that figure. Grooves 15 are made in cover plate 3', to form guides during contact with the adjacent vertebra and take care of imparting increased strength to the connection when tension screws 11 and 12 of FIG. 2 are tightened.

Figure 4:
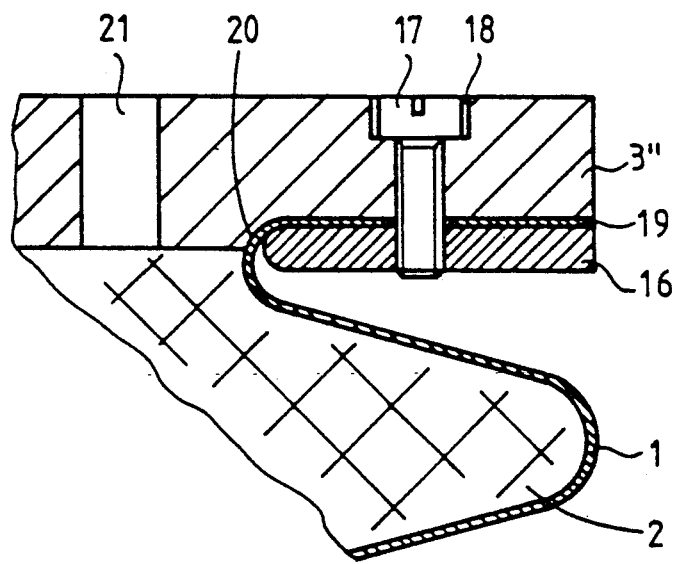

FIG. 4 shows part of another variation of the embodiment which forms, for example, a modification of the embodiment shown in FIG. 1. Here, corrugated tube 1 is connected with cover plate 3'' by means of a clamping ring 16 which is configured as a divided ring in whose thread engages a screw 17 that has been inserted from the exterior face of the cover plate and whose head is supported in a corresponding recess 18 accommodating the head of the screw. The edge region 19 of corrugated tube 1 is thus clamped in between the underside of cover plate 3''' which is there provided with a region 20 shaped as a partial recess in clamping ring 16 and can thus be installed easily The strength of the connection is ensured under all stresses to be expected.

A passage opening 21 in cover plate 3'' serves to fill the interior with viscoelastic material—or, together with a similar opening, as ventilation.

The present invention is not limited in its embodiments to the above-described preferred embodiment. Rather, a number of variations are conceivable which take advantage of the described solution even for basically different configurations.

It will be understood that the above description of the present invention is susceptible to various modifications, changes and adaptations, and the same are intended to be comprehended within the meaning and range of equivalents of the appended claims.

What is claimed is:

1. An intervertebral disk endoprosthesis filled with viscoelastic material and provided with cover plates at its end faces, comprising a circular or elliptical corrugated tube surrounding and contiguous with the viscoelastic material and terminated by the cover plates, wherein said cover plates are rigid, and wherein said corrugated tube allows for less constrained tilting of said cover plates, and further accommodates the compressive bulging of said viscoelastic material.

2. Endoprosthesis as defined in claim 1, wherein the corrugated tube is composed of biocompatible metal.

3. Endoprosthesis as defined in claim 1, wherein the viscoelastic material is filled completely or partially with oriented or unoriented fibers.

4. Endoprosthesis as defined in claim 3, wherein the filling is inhomogeneous, such that compressibility increases in the direction toward at least one edge region.

5. Endoprosthesis as defined in claim 1, wherein the viscoelastic material includes hardenable, originally liquid, components.

6. Endoprosthesis as defined in claim 5, wherein at least one of the cover plates and the corrugated tube are provided with at least one of a closable fill opening and a ventilation opening.

7. Endoprosthesis as defined in claim 1, wherein the corrugated tube is fastened to at least one cover plate by a screwable clamping device.

8. Endoprosthesis as defined in claim 7, wherein the clamping device is a clamping ring.

9. Endoprosthesis as defined in claim 1, wherein the corrugated tube is welded to at least one cover plate.

10. Endoprosthesis as defined in claim 1, wherein the a corrugated tube has a wall thickness which is variable in one of a transverse direction or the longitudinal direction.

11. Endoprosthesis as defined in claim 1, wherein at least one of the outwardly oriented end faces of the cover plate is provided with at least one of spurs, radial grooves, and circumferential grooves.

12. Endoprosthesis as defined in claim 1, wherein at least one of the outwardly oriented end faces of the cover plates and of the corrugated tube is provided with at least one of a porous, surface area enlarging coating, surface configuration, and surface regions.

13. Endoprosthesis as defined in claim 1, wherein at least one of the outwardly oriented frontal and side faces is provided with embedments of a bioactive material.

14. Endoprosthesis as defined in claim 13, wherein the bioactive face is composed of at least one of hydroxyl apatite, polylactide or HIP material.

15. An intervertebral disk endoprosthesis filled with viscoelastic material and provided with cover plates at its end faces, comprising a circular or elliptical corrugated tube surrounding and contiguous with the viscoelastic material and terminated by the cover plates, wherein at least one of said cover plates is provided with a flange, and wherein said corrugated tube allows for less constrained tilting of said cover plates, and further accommodates the compressive bulging of said viscoelastic material.

16. Endoprosthesis as defined in claim 15, wherein the flange extends parallel to the center axis of the corrugated tube.

17. Endoprosthesis as defined in claim 16, wherein the flange is provided with a bore.

18. Endoprosthesis as defined in claim 17, wherein the direction of the bore diverges from the cover plate toward the center axis of the corrugated tube so that a screw passing through the bore constitutes a tension screw.

19. Endoprosthesis as defined in claim 17, wherein, on the side facing away from the center axis of the corrugated tube, the bore is provided with a recess for a screw head.

20. Endoprosthesis as defined in claim 15, wherein the exterior face of the cover plate is provided with grooves which are oriented perpendicularly to the flange.

21. Endoprosthesis as defined in claim 1, wherein the exterior of at least one of the cover plates is configured in such a way that it is adapted to the end faces of an adjacent vertebra.

* * * * *